(12) United States Patent
McAdams et al.

(10) Patent No.: US 6,731,987 B1
(45) Date of Patent: May 4, 2004

(54) ELECTRODE FOR THE TRANSFERRING AN ELECTRIC CURRENT THROUGH A PATIENT'S SKIN

(75) Inventors: Eric Thomas McAdams, Antrim (GB); Dao Min Zhou, Castaio, CA (US); Pascal Andre Nicolas Muller, Grenoble (FR); Claude Mikler, Dijon (FR)

(73) Assignee: IOMED, Inc., Salt Lake City, UT (US)

( * ) Notice: Subject to any disclaimer, the term of this patent is extended or adjusted under 35 U.S.C. 154(b) by 0 days.

(21) Appl. No.: 09/831,318
(22) PCT Filed: Nov. 8, 1999
(86) PCT No.: PCT/FR99/02726
§ 371 (c)(1), (2), (4) Date: Apr. 25, 2002
(87) PCT Pub. No.: WO00/27467
PCT Pub. Date: May 18, 2000

(30) Foreign Application Priority Data

Nov. 9, 1998 (FR) .......................................... 98 14072

(51) Int. Cl.$^7$ ................................................. A61N 1/04
(52) U.S. Cl. ...................... 607/152; 600/396; 600/372
(58) Field of Search .............................. 600/372, 382, 600/384, 391, 392, 395, 396, 397; 607/152; 604/890.1

(56) References Cited

U.S. PATENT DOCUMENTS

| | | | |
|---|---|---|---|
| 4,736,752 A | 4/1988 | Munck et al. | |
| 4,776,350 A | 10/1988 | Grossman et al. | |
| 5,456,710 A | 10/1995 | Gadsby | |
| 6,019,877 A | * 2/2000 | Dupelle et al. ............. | 607/152 |

FOREIGN PATENT DOCUMENTS

| WO | WO 98/26760 | 6/1998 |
|---|---|---|
| WO | WO 98/39057 | 9/1998 |

* cited by examiner

*Primary Examiner*—Scott M. Getzow
(74) *Attorney, Agent, or Firm*—Factor & Lake

(57) ABSTRACT

The electrode comprises a) a layer (5) which conducts electricity for the supply or the collection of an electrical current traversing the electrode, and b) a consumable electrochemical interface layer (7). According to the invention, it comprises, in addition, an intermediate layer (6) made of a chemically inert and electrically resistant material. This layer can consist of a dispersion of fine particles of carbon in a polymer binder.

Application in the preparation of electrodes with increased electrochemical capacity, for an ionophoresis device for the transdermal administration of drugs or a device for the electrocicatrization of wounds.

18 Claims, 1 Drawing Sheet

ELECTRODE FOR THE TRANSFERRING AN ELECTRIC CURRENT THROUGH A PATIENT'S SKIN

BACKGROUND OF THE INVENTION

The present invention relates to an electrode for the transfer of an electrical current traversing a patient's skin, and more particularly, to such an electrode of the type which comprises a) an electricity conducting layer for the supply or the collection of said electrical current traversing the skin, and b) a consumable electrochemical interface layer.

Electrodes of this type are used in various medical applications, such as the recording of electrical signals originating from the human or animal body (electrocardiogram, electroencephalogram, etc. . . . ), the transdermal administration of a drug by ionophoresis or the electrocicatrization of wounds or injuries.

The devices designed to use these applications normally comprise two electrodes, one functioning as anode and the other as cathode, both placed in contact with the skin, where the current applied, or to be recorded, passes between these two electrodes.

Each electrode is formed in the standard way of a metal conducting layer, for example, made of silver, associated with (or glued to), an ionic conduction layer consisting of a gel in contact with the patient's skin, where this gel is either charged with an electrolyte ensuring a good electrical contact between the skin and the silver layer (in the case of the recording of electrical signals originating from the human or animal body, for example) or it is charged with an active substance in ionic form (in the case of the transdermal administration of drugs by ionophoresis).

In the case of electrocicatrization of wounds or injuries, said ionic conduction layer associated with the conducting layer is a hydrophilic layer which in this case is in contact with the wound to be treated.

This hydrophilic layer is either a layer which was either initially rendered conducting, that is before its application to the wound, or immediately after the application, by a charge of water and mineral salts, or it is a dry hydrophilic layer which is nonconducting during its application to the skin, and then becomes conducting due to the migration of the exudates of the wound into the thickness of the said dry hydrophilic layer.

In this case, the dry hydrophilic layer which constitutes the ionic conducting layer can be prepared from any dry hydrophilic absorbing material of composition used in the preparation of dressings intended for the treatment of exudating wounds.

It can also be in the form of absorbing foams, in particular hydrophilic foams of polyurethane used in so called hydrocellular dressings, in the form of fibers based on absorbing materials such as, for example, alginate fibers, such as sodium or calcium alginates, or fibers of cellulose derivatives, in the form of compresses made of nonwoven materials, in the form of lyophilized gels and in the form of hydrocolloid compositions such as gels or hydrocolloid compositions, such as those used in dressings of the so called hydrocolloid type.

In all cases, the electrical conduction passes from electronic conduction (in the layer of silver) to ionic conduction (in the gel). The transfer of charge that allows this exchange is controlled by the electrochemical properties of the electrode/skin interface.

To ensure the stability of these electrochemical properties, it has been suggested to form on the above mentioned layer of silver an electrochemical interface layer which is such that it facilitates the passage from ionic conduction to electrochemical conduction by maintaining, at the interface in question, a weak and stable electrochemical potential, ensuring a high-yield charge transfer.

This interface layer, also called "sacrificial" layer, conventionally consists of silver or a mixture of Ag/AgCl, in the case of an anode or a cathode, respectively, deposited on, or mixed with, the current supplying layer. The electrochemical interface specific for these sacrificial layers is then provided by the reversible redox reaction:

$$Ag + Cl^- \leftrightarrows AgCl + e^-$$

which transforms, by oxidation, the silver of the anode into silver chloride and, by reduction, the silver chloride of the cathode into silver. The potential of the reaction is relatively weak (approximately 100–200 mV) compared to the potential of the standard hydrogen electrode. The difference in potential between the anode and the cathode is weak and of the same order of magnitude. In addition, because the standard potential of the Ag/AgCl pair is located in the window of electrochemical stability of the water, this reaction prevents any phenomenon of electrolysis of the water, and the accompanying variations in pH and formation of gas, and thus ensures the electrochemical stability of the interface and the safety of the patient with respect to one of the hazards connected with the drifting of the electrochemical interface, and this for as long as said reaction can take place, that is as long as silver chloride is present at the cathode and/or as long as silver and the Cl⁻ ion are available at the anode.

Although such interface layers thus meet the requirement as far as the electrochemical stability of the electrode/skin interface is concerned, it was observed that, when the treatment requires the passage of strong currents for long periods of time, as is the case in the ionophoretic devices for transdermal administration of drugs, electrodes equipped with such interface layers still were unsatisfactory with regard to their resistivity to physical-degradation, the uniformity of the density of the current on the surface of the electrode, and the "electrochemical capacity" of the latter, that is its ability to deliver a current with a given intensity (on the order of 1 $\mu$A to 1 mA, more specifically on the order of 0.2 mA per $cm^2$ of electrode surface in the case of application in ionophoresis) for a given time interval (of several hours or more) as is required to ensure precise control of a transdermal administration of a drug by ionophoresis.

Indeed, one observes, in this application, some dislocation of the electrode, notably due to a deficiency in the adherence of the layer of Ag/AgCl to the underlying layer of silver. One also observes the absence of uniform density of the current traversing adjacent areas of the electrode, where this density tends to increase on the edges of the electrode. This deficiency of uniformity creates "hot spots" on these edges which irritate the patient's skin. In addition, it causes a more rapid erosion of the electrochemical interface layer at places perpendicular to the hot spots of the electrode, whose life span is then decreased. This decrease results in a decrease of the electrochemical capacity of the electrode.

SUMMARY OF THE INVENTION

The present invention precisely has the purpose of providing an electrode of the above described type, which is improved so as to present a superior mechanical stability and electrochemical capacity, compared to those of the electrodes of the prior art, that is a life span which is compatible with the duration of the therapeutic treatments which use such electrodes, such as transdermal administration of drugs by ionophoresis, or electrocicatrization.

These purposes of the invention have been achieved, as well as others which will become apparent in a reading of the following description, with an electrode for the transfer of an electrical current traversing a patient's skin, of the type which comprises a) an electricity conducting layer for the supply or the collection of said electrical current traversing the skin, and b) a consumable electrochemical interface layer, this electrode being remarkable in that it comprises, between said conducting layer and said electrochemical interface layer, c) an intermediate layer made of a chemically inert and electrically resistant material.

As will be shown in detail below, the presence of this intermediate layer simultaneously improves the mechanical resistivity of the electrode and its electrochemical capacity.

According to a preferred embodiment variant of the invention, the intermediate layer comprises carbon, for example, in the form of fine particles dispersed in a polymer binder.

According to another preferred embodiment variant of the invention, the electrode is formed on a substrate made of an electrochemically insulating material to which the electricity conducting layer is glued.

According to yet another preferred embodiment variant of the invention, the electrode in addition comprises an ionic conduction layer in contact with a patient's wound or skin.

According to an optional characteristic of the electrode according to the invention, the latter in addition comprises a layer made of an electrically insulating material, which covers the edges of the stack of layers formed by the conducting layer, the intermediate layer and the electrochemical interface layer.

According to yet another optional characteristic of the electrode according to the invention, the conducting layer is in the form of a grid.

BRIEF DESCRIPTION OF THE DRAWINGS

Other characteristics and advantages of the present invention will become apparent after a reading of the following description and examination of the drawing in the appendix in which.

DETAILED DESCRIPTION OF THE INVENTION

Figure 1:
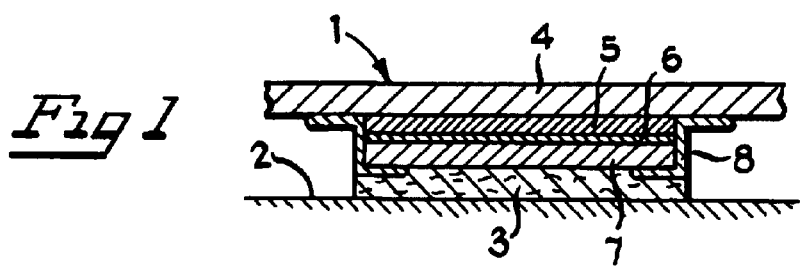
FIG. 1 is a diagrammatic cross section of an electrode according to the invention, applied to a patient's skin.

Reference is made to FIG. 1 of the drawing in the appendix which shows a diagrammatic representation of an embodiment variant of the electrode 1 according to the invention, in the position which it occupies on a patient's skin 2. In this FIG. 1, the electrode is shown in an exploded view of its thickness to better show the different layers of materials which constitute it. Below, the description of the electrode as an element of an ionophoretic device for the transdermal administration of drugs is only as an illustrative and nonlimiting example; such an electrode can be used in other devices, as will be seen below.

An ionophoresis device for the transdermal administration of drugs conventionally comprises an electronic circuit designed to deliver a current with predetermined intensity for a predetermined time interval, between two electrodes applied to a patient's skin. One of the electrodes itself is glued to a "reservoir," referenced by the numeral 3 in FIG. 1, in direct contact with said patient's skin, where this reservoir contains, in solution, an ionic form of an active substance constituting the drug to be administered. Depending on the polarity of this ionic form, the electrode in question is an anode or a cathode, the electrical field established by the circulation of the current between the two electrodes forcing the ions of the active ingredient to pass from the reservoir 3, consisting of an ionic conduction layer formed of a hydrophilic gel charged with a saline solution of said active substance, for example, on the adjacent part of said patient's skin.

This electrode itself can also be glued to a layer of hydrophilic gel charged with a saline solution, for the only purpose of ensuring a good electrical conduction between the skin and the electrode, as required for the passage of the current between these two.

Each of the two layers of gel can be integrated in one of the electrodes and "hydrated" with the above described solutions, immediately before the start up of a treatment.

Figure 2:
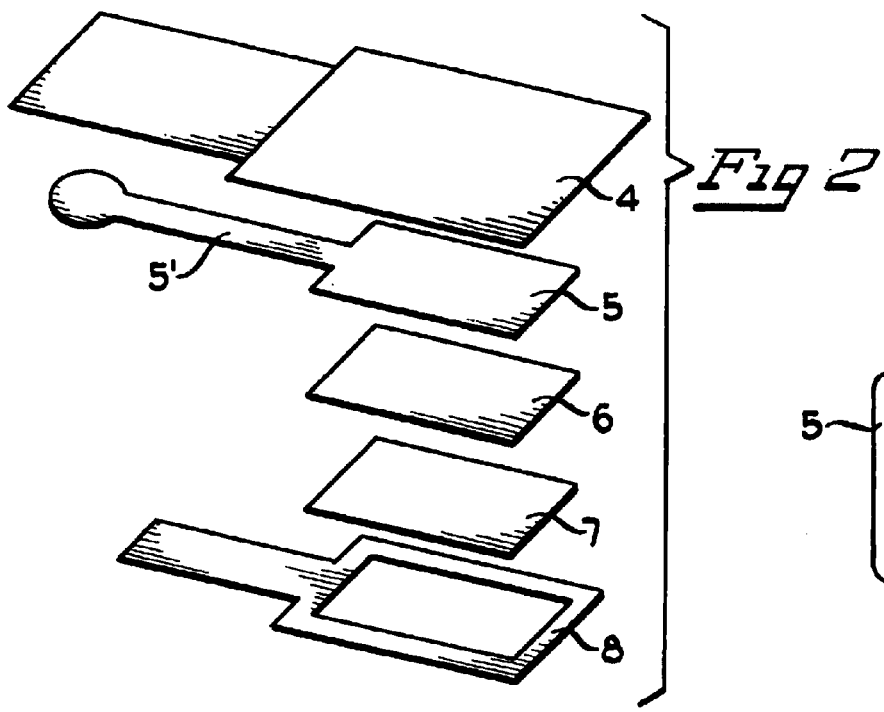
FIG. 2 is an exploded view of the electrode of FIG. 1.

In FIGS. 1 and 2 of the drawing in the appendix, it is thus apparent that the electrode according to the invention comprises several layers of different materials, glued one to the other. Thus, the electrode can comprise, first, a layer 4 of a substrate, which is advantageously flexible, coated on one side with a layer 5 made of an electricity conducting material. The flexibility of the substrate allows a close application of the electrode to the patient's skin.

According to the present invention, layer 5 itself is covered with a layer 6 made of an electrically resistant, chemically inert, material which is intermediate between the conducting layer 5 and the consumable electrochemical interface layer 7, of the type described in the preamble of the present description.

The stack of layers 5, 6, 7 described above, can be covered, on its edges, by a layer 8 made of a dielectric material which forms a frame for a purpose which will be explained below.

Electrode 1 so formed can be completed by the deposition, on the layers 7 and 8, of the layer of gel 3 mentioned above.

Various well known techniques for the preparation of thin films or layers of materials can be used to deposit the above mentioned layers, vapor phase deposition in a vacuum, coating with a roller, serigraphic deposition, etc. . . . The latter technique is preferred for the preparation of the electrode of FIGS. 1 and 2.

From the above, it results that the electrode according to the invention differs essentially from the known techniques of the prior art by the presence of layer 6 made of an electrically resistant and chemically inert material.

According to an embodiment variant of the invention, this layer 6 is a layer based on fine carbon having resistivity, having a thickness of a few millimeters, consisting, for example, of a dispersion of fine particles of carbon in a polymer binder. These particles can have a size of 0.1–5 μm, the carbon content of the ink being on the order of 15–25 wt % of the mixture.

According to another embodiment variant of the invention, layer 6 has anisotropic resistivity. An appropriate material to form constitute such a layer is, for example, the material sold under the name of "z-axis adhesive film" by the USA Minnesota Mining and Manufacturing Co.

The layer 6 is interposed between the layer 5, made of silver, for example, and the interface layer 7 which is made of Ag/AgCl for the cathode, and of silver for the anode, where this layer 7 itself is in direct contact with the layer 3 of hydrophilic gel charged with an ionic electricity conducting solution.

The layer 5 ensures the electrical connection with the electronic circuit which controls the passage of an electric current between such electrodes. The layer 7 ensures the stability of the electrochemical interface properties of the electrode with respect to the layer of gel and the patient's skin.

The intermediate layer 6, consisting, for example, of carbon, of the electrode according to the invention first of all functions, thanks to its chemical inertia, as a "buffer layer" which ensures:

1) that the adhesion between the layers 5 and 7 is not affected by the passage of the current and the depletion of the "sacrificial" layer of Ag/AgCl in the case of a cathode or of silver in the case of an anode,
2) that the conductivity of the layer 5 is not affected by the electrochemical reactions which develop in the electrical interface layer 7, and
3) that the adhesion of the layer 5 to the substrate 4 is not deteriorated by these electrochemical reactions.

According to the present invention, the intermediate layer 6 must also present a higher electrical resistivity than that of the underlying conducting layer 5. Measurements have indeed shown that the result is a more uniform distribution of the current on the surface of the sacrificial layer 7, which attenuates "the edge effect," noted in the preamble of the present description, in the absence of the layer made of carbon. The result is a more regular "consumption" of the sacrificial layer 7, as a current passes, which increases the life span of the electrode. The latter is then capable of causing the circulation under a patient's skin of a current having a given intensity, for a longer time period than an electrode which lacks the layer 6 made of carbon, which increases the "electrochemical capacity" of the electrode according to the invention in comparison to that of an electrode which lacks this layer 6.

Thus, it is apparent that the present invention indeed achieves the purposes stated in the preamble of the present description, namely to provide an electrode which presents, on the one hand, improved mechanical and electrochemical stability, and, on the other hand, improved electrochemical capacity.

The results stated above are further strengthened thanks to the insulating layer 8 which notably coyers the edges of the underlying layers 5, 6 and 7. Incidentally, it should be noted that this layer also serves the function of insulating, by covering it, a power supply track 5' of the layer 5, extending over the edges of the contour of this layer.

The layer 8 protects the layers 5 and 6 of the layer of gel 3 and thus prevents a solvent contained in this layer from penetrating, by at the edges, into the layer 5, and thus minimizes the risks of "delamination" of the layers 5 and 6.

This electrically insulating layer 8 thus acts against the presence of areas with high current density on the edges of the electrode, which creates "hot spots" which are unpleasant for the patient due to the irritation of the skin which they can generate, and detrimental to the electrochemical capacity of the electrode by the early erosion of the sacrificial layer which they cause.

The embodiment variant of the electrode according to the invention described below is only an illustrative and non-limiting example.

EXAMPLE

The substrate layer 4 used to support the other layer consists of a film of polyester having a thickness of approximately 50 μm.

The layers 5, 6, 7 are deposited successively on the substrate 4 by the well known technique of serigraphy.

Figure 3:
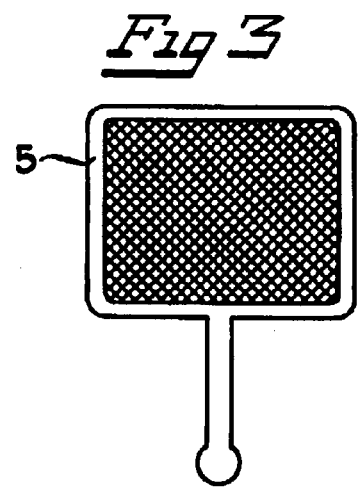
FIG. 3 is a diagrammatic view of an embodiment variant of a current supply layer forming part of the electrodes of FIGS. 1 and 2.

The layer 5 can consist of any conducting "ink," typically an ink based on silver, which is capable of simultaneously presenting a good adhesion to the substrate 4 and to the intermediate layer 6 which covers it. The layer 5 can present a network of gaps or "holes," as represented in FIG. 3, so as to form a grid. These gaps allow the layer 6 to adhere directly to the substrate, which improves the mechanical stability of the electrode and creates a multitude of curvatures in the lines of current supply, which ensure a better distribution of said current because of the multiplication of the edge effects. The deformations which this grid imparts to the layers 6 and 7 which cover it an increase in the surface area of the layer 7/gel 3 interface, or the layer a 7/electrolyte interface, which is favorable to the electrical properties of this interface.

The intermediate layer 6 must have resistivity and be thin, or it must have anisotropic resistivity, and be chemically inert. To form the intermediate layer, on can use a commercially available conducting ink based on fine particles of carbon dispersed in a polymer binder and a solvent. Such inks are marketed by the companies DuPont de Nemours, Acheson Colloiden BV or Gwent Electronic Materials, for example. Other materials having resistivity can be used to form the layer 6: an ink based on graphite, such as the one marketed under the name of BIROX by the company DuPont de Nemours, inks based on ruthenium, palladium, thallium or iridium oxides, an ink based on palladium, or a palladium-silver alloy. The ink must present the required adhesion properties and it must allow the physical separation of the sacrificial layer 7 from the conducting layer 5 made of silver. When the layer 7 is made of Ag/AgCl, the layer 6 ensures that the adhesion of the latter layer to the underlying layers is not affected by the passage of the current and the resulting depletion of AgCl of the layer 7, that the electrical conducting properties of the layer 5 are not affected by the electrochemical reactions which develop on the other side of the layer 6, and that the substrate 4 itself is not affected by said reactions. It is preferred for the intermediate layer to have a thickness of 1–100 μm, preferably 5–10 μm, in the case of a thin layer having resistivity.

The sacrificial layer 7 conventionally consists, as seen above, of an ink based on silver for the anode, and an ink based on Ag/AgCl for the cathode. For the same ink, the thickness and the roughness of this layer of cathode essentially determines the electrochemical capacity as defined above, that is the useful life of the latter. To confer to this layer the thickness which is appropriate to achieve the desired life span, one can construct it using a screen having large meshes or by superposing several layers deposited in succession.

The dielectric layer 8 is made of an insulating ink, for example, a UV hardenable ink for thick films having the reference 451ss in the catalogs of the Dutch company ACHESON COLLOIDEN BV.

Electrodes were prepared according to the above indicated data. The layers 5, 6, 7, 8 presented thicknesses of 5–20 μm, 5–10 μm, 20–70 μm, and 5–20 μm, respectively. It is preferred for the layers 5, 6, 7, 8 to present thicknesses of 12 μm, 8 μm, 40 μm and 8–10 μm, respectively. The composition of the layer 7 for a cathode was 40–80 wt % of AgCl and 60–20 wt % of silver, and, more advantageously, 30–40 wt % of Ag and 60–70 wt % of AgCl.

Figure 4:
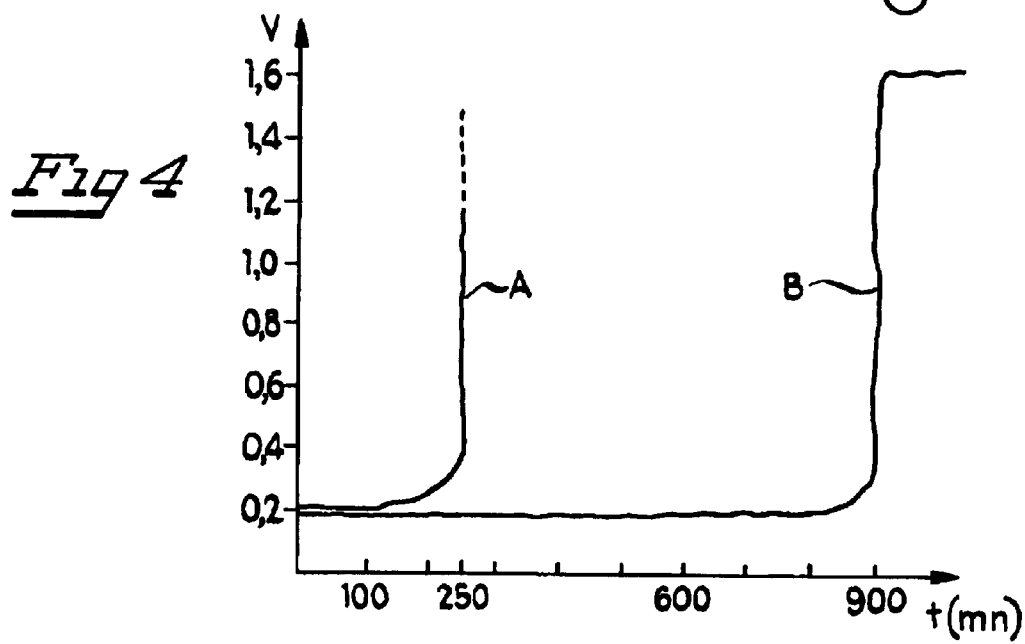
FIG. 4 represents graphs which illustrate the increase in the electrochemical capacity of the electrode according to the invention, compared to that of an electrode of the prior art.

The graphs of FIG. 4 illustrate the increase in the electrochemical capacity obtained by the present invention. They present the variation over time of the voltage recorded between the layer 5 and an electrolyte bathing the layer 7 or the layer of gel 3, when one applies to the electrode a current of 1 mA. The graphs A and B represent the variation of this voltage for an electrode which lacks the layer 6 made of carbon and for an electrode according to the invention, respectively. In the two cases, one starts by recording a voltage on the order of 0.2 V corresponding to the low electrochemical potential of the reversible redox reaction generated by the presence of the sacrificial layer 7. After a certain time period, the latter layer is depleted, and the electrochemical potential changes to a much higher value, on the order of 1.6 V, that is the electrochemical potential of the reaction of electrolysis of the water, the solvent of the electrolyte. At this time, the electrode is degraded and it can no longer be used.

Routinely a time of 250/300 min is observed before this voltage appears, using an electrode which lacks the layer 6 made of carbon (graph A) and has a current density of 125 $\mu A/cm^2$.

The presence of a layer 6 consisting of a DuPont ink having the numeral E 84380-106A increases this time to at least approximately 900 min (graph B), with the same current density, and this without the observation of fissures and separation of the above mentioned layers.

The "electrochemical capacity" Q of the electrode according to the invention as a result is increased by as much, passing from a value centered about approximately 40 $mA·min/cm^2$, to a surface area of the electrode being measured in $cm^2$, according to one of the objectives pursued by the present invention.

Naturally, the invention is not limited to the embodiment variant which has been described and represented, and which was only given as an example. Thus, the different layers of the electrode according to the invention could be prepared by coating methods other than serigraphy. Thus, one can find commercial substrates charged with carbon which impart to these substrates a certain electrical resistivity which allows them to function as the intermediate layer 6. One then forms, on one face of this substrate, a metal layer, for example, by vapor deposition, to constitute the layer 5 and, on the other face of the substrate, the electrochemical interface layer 7.

Similarly, the invention is not limited to the preparation of electrodes for ionophoretic devices for transdermal administration of drugs. On the contrary, it can be applied anywhere where an electrochemical equilibrium must be maintained at the interface to which the electrode is applied, and thus, notably, in electrodes used for electrotherapy of wounds or injuries, electrodes for the detection of electrical signals originating from the human body (electroencephalograms, electrocardiograms) and in electrodes for the transdermal muscle electrostimulation (TENS).

What is claimed is:

1. Electrode for the transfer of an electrical current through a patient's skin, of the type which comprises:
   a) a layer (5) which conducts electricity to supply or collect said electrical current traversing said skin, and
   b) a consumable layer (7) of electrochemical interfacing, characterized in that it comprises, between said conducting layer (5) and said electrochemical interface layer (7),
   c) an intermediate layer (6) made of a chemically inert and electrically resistant material, which completely separates the layer and the consumable layer.

2. Electrode according to claim 1, characterized in that the intermediate layer (6) comprises carbon.

3. Electrode according to claim 2, characterized in that the intermnediate layer (6) consists of fine particles of carbon dispersed in a polymer binder.

4. Electrode according to claim 1, characterized in that said layer (6) has a thickness between approximately 1 μm and 100 μm, preferably between 5 and 10 μm.

5. Electrode according to claim 1, characterized in that it comprises, in addition, an ionic conduction layer (3) in contact with said skin.

6. Electrode according to claim 5, characterized in that said ionic conduction layer (3) is in contact with a wound and it consists of a dry hydrophilic layer which does not conduct electricity at the time of its application to the wound and which becomes conducting due to the migration of the exudates of the wound into the thickness of said dry hydrophilic layer.

7. Electrode according to claim 5, characterized in that said ionic conduction layer (3) is in contact with a wound and it is made conducting before its application to the wound by a charge of water and mineral salts.

8. Electrode according to claim 1, characterized in that it comprises, in addition, a layer (8) made of an electrically insulating material, which covers the edges of the stack of layers consisting of the conducting layer (5), the intermediate layer (6), and the electrochemical interface layer (7).

9. Electrode according to claim 1, characterized in that the conducting layer (5) is in the form of a grid.

10. Electrode according to claim 1, characterized in that it is formed on a substrate (4) made of an electrically insulating material to which the electricity conducting layer (5) is glued.

11. Electrode according to claim 1, characterized in that the intermediate layer (6) consists of a substrate material charged with carbon particles.

12. Electrode according to claim 1, characterized in that said intermediate layer presents an anisotropic resistivity.

13. Electrode according to claim 1, characterized in that the conducting layer (5) comprises silver.

14. Electrode according to claim 1, characterized in that the electrochemical interface layer (7) comprises silver.

15. Electrode according to claim 1, characterized in that the electrochemical interface layer (7) comprises a mixture of Ag/AgCl.

16. Electrode according to claim 15, characterized in that said mixture comprises 40–80 wt % of AgCl and 60–20 wt % of silver, preferably 30–40 wt % of Ag and 60–70 wt % of AgCl.

17. Electrode according to claim 1, characterized in that it presents an electrochemical capacity of at least 168 $\mu A·min·cm^2$.

18. Use of an electrode according to claim 1, in a device of the group formed by an iontophoretic device for the transdermal administration of drugs, a device for the electrocicatrization of wounds, a device for collection of electrical signals emitted by the human or animal body, and a device for transdermal muscle electrostimulation.

* * * * *